United States Patent [19]

Wedemeyer et al.

[11] 4,304,940
[45] Dec. 8, 1981

[54] PREPARATION OF 2-ALKYL- AND 2-ARYL-THIOMETHYLPHENOLS

[75] Inventors: Karlfried Wedemeyer, Cologne; Helmut Fiege, Leverkusen, both of Fed. Rep. of Germany

[73] Assignee: Bayer Aktiengesellschaft, Leverkusen, Fed. Rep. of Germany

[21] Appl. No.: 181,593

[22] Filed: Aug. 27, 1980

[30] Foreign Application Priority Data

Sep. 12, 1979 [DE] Fed. Rep. of Germany ....... 2936803

[51] Int. Cl.³ .............................................. C07C 148/00
[52] U.S. Cl. ........................................ 568/45; 568/51; 568/52
[58] Field of Search ............................. 568/45, 51, 52

[56] References Cited

U.S. PATENT DOCUMENTS

3,553,270  1/1971  Wollensak et al. ................... 568/51
3,903,173  9/1975  Eggensperger et al. .............. 568/51

FOREIGN PATENT DOCUMENTS

1499043  1/1978  United Kingdom ................... 568/51

*Primary Examiner*—Donald G. Daus
*Assistant Examiner*—M. C. Eakin
*Attorney, Agent, or Firm*—Sprung, Felfe, Horn, Lynch & Kramer

[57] ABSTRACT

In the preparation of a 1-alkyl- and 2-aryl-thio-methyl-phenol of the formula

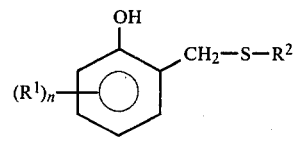

in which
  $R^1$ is, or the radicals $R^1$ are, in the 3-, 5- and/or 6-positions relative to the hydroxyl group and each independently is a hydrogen or halogen atom, or an alkyl, cycloalkyl, aryl, aralkyl or alkoxy group,
  n is 1, 2, or 3, and
  $R^2$ is an optionally substituted alkyl group having 1 to 12 carbon atoms, an optionally substituted cycloalkyl group having 3 to 6 carbon atoms, an optionally substituted phenyl radical or an optionally substituted aralkyl radical,
by reacting a phenol of the formula

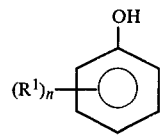

with formaldehyde or an formaldehyde producing compound and with a mercaptan or a thiophenol of the formula $$R^2-S-H.$$

the improvement which comprises effecting the reaction at a temperature of about 90° to 220° C. in the presence of at least one compound of lithium, magnesium, calcium, strontium, barium, zinc, cadmium, lead, manganese, cobalt, nickel, cooper, iron, chromium and aluminum as a catalyst. The products are obtained in high yield and selectivity.

9 Claims, No Drawings

PREPARATION OF 2-ALKYL- AND 2-ARYL-THIOMETHYLPHENOLS

The invention relates to an unobvious process for the preparation of certain 2-alkyl- and 2-aryl-thiomethylphenols.

Compounds of this type are used, for example, as intermediates in the preparation of plant protection agents.

It is known that an alkylthiomethyl group can be introduced into the free para- or ortho-position of 2,6- or 2,4-dialkylphenols respectively, by reaction with mercaptans and formaldehyde in the presence of 0.1 to 1 mole of a strong base (such as potassium hydroxide) per mole of dialkylphenol. In the case of alkylphenols having a free- ortho- and para-position, on the other hand, the alkylthiomethyl group simultaneously enters both the ortho-position and the para-position of the phenol nucleus [see DAS (German Published Specification) 1,593,821, Deutsche Advance 1967]. The selective introduction of the alkylthiomethyl group into the ortho-position of phenols having a free para-position, by reaction with formaldehyde and a mercaptan, is not described.

It is further known that α-aryl- or α-alkylthiomethyl-naphthols are obtained, for example, by reacting β-naphthol with formaldehyde and aryl- or alkylmercaptans (see F. POPPELSDORF and S. J. HOLT, J. Chem. Soc. 1954, 1,124 et seq.). However, the reaction only proceeds when considerable amounts of triethylamine (0.5 mole/mole of phenol) are simultaneously present as an auxiliary base, and even then it still requires reaction times of about 6 days in order to achieve satisfactory yields.

If this reaction is applied to phenol, which is known to possess three reactive sites, a reaction mixture is formed which contains considerable amounts of isomeric 4-aryl or 4-alkyl-thiomethylphenol and also homologues and resins, in addition to the desired 2-aryl or 2-alkyl-thiomethylphenol. As a result, not only is the yield of 2-aryl or 2-alkyl-thiomethylphenol greatly reduced, but its isolation is also hindered to such an extent that it can not be carried out economically on an industrial scale.

For this reason the starting material used in the known industrial processes for the preparation of 2-alkylthiomethylphenols is a 2-dimethylaminophenol (a MANNICH base),

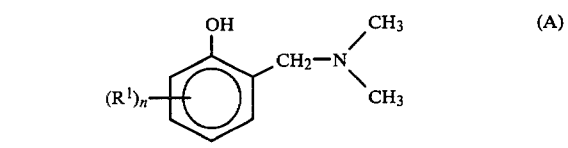

a 2-chloromethylphenol

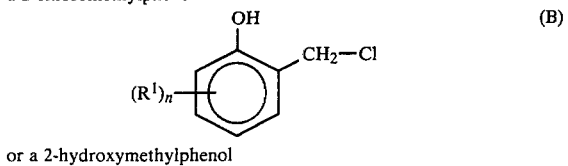

or a 2-hydroxymethylphenol

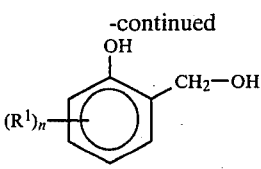

which is reacted with the corresponding mercaptans or mercaptan-producing compounds [literature for the reaction of compound (A), see, for example, DAS (German Published Specification) 2,614,875 BAYER AG; of (B): DT-PS (German Patent) No. 1,910,588, BAYER AG: Japanese Pat. No. 74 20 191; and C.A. 82, 86 197 x; and of (C) German Application P 2838273.2. The disadvantage of these processes lies in particular in the fact that the compounds (A), (B) or (C) are not readily available and must be prepared beforehand at considerable expense in terms of time, material and technical aids.

It was thus very desirable to find a process which avoids the troublesome preparation involved in these preliminary stages and makes it possible selectively to prepare 2-alkyl and 2-aryl-thiomethylphenols of the following formula (I) in one step, by directly reacting the appropriate phenols with formaldehyde and a mercaptan. Such a process is novel.

The present invention now provides a process for the preparation of a 2-alkyl- or 2-aryl-thiomethylphenol of the general formula

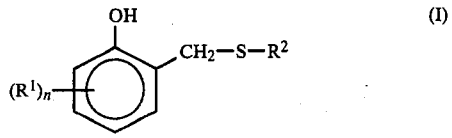

in which
n is 1, 2 or 3,
$R^1$ is, or the radicals $R^1$ are, in the 3-, 5- and/or 6-position relative to the hydroxyl group and independently of one another denote a hydrogen atom, an alkyl, cycloalkyl, aryl, aralkyl or alkoxy group or a halogen atom, and $R^2$ represents an optionally substituted alkyl group having 1 to 12 carbon atoms, an optionally substituted cycloalkyl group having 3 to 6 carbon atoms, an optionally substituted phenyl radical or an optionally substituted aralkyl radical, comprising simultaneously reacting a phenol of the general formula

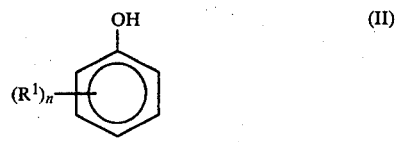

with formaldehyde or a formaldehyde-producing compound and with a mercaptan or thiophenol of the general formula $$R^2-S-H \qquad (III)$$

characterised in that the reaction is carried out at a temperature of about 90° to 220° C., in the presence of one or more of lithium, magnesium, calcium, strontium, barium, zinc, cadmium, lead, manganese, cobalt, nickel, copper, iron, chromium and aluminum compounds as a catalyst. The compounds of formula (I) can be obtained with a high selectivity and yield by the process of the present invention.

In view of the state of the art, it is surprising that, in the process according to the invention, 2-alkylthiomethylphenols can be formed in good yields with such a high selectivity:

It is known that metal cations with a high valence and/or a small ionic radius favor the reaction of phenol with formaldehyde to give 2-hydroxymethylphenol [see D. A. FRASER et al., J. appl. Chem. 7 (1957), 676–700]. It was also known that 2-hydroxymethylphenol can be reacted with alkyl- or aryl-mercaptans to give the corresponding 2-alkyl- or 2-aryl-thiomethylphenols [see German Application P 28 38 273.2, which does not yet form part of the state of the art]. However, if the reaction of phenol with formaldehyde, in the presence of such metal cations, is carried out at the temperatures according to the invention, namely above 90° C., the 2-hydroxymethylphenol further reacts very rapidly, and extensively with itself and with the phenol which is still present, to give phenol-formaldehyde resins (so-called novolaks) [see D. A. FRASER et al., J. appl. Chem. 7 (1957), 676–700]. It was therefore also to be expected that such resinification reactions would predominate under the conditions according to the invention, so that considerable prejudice would have to be overcome in order to carry out the reaction at such high temperatures.

If the reaction of phenol with formaldehyde and the mercaptan, in the presence of the catalysts according to the invention, is carried out at lower temperatures than the temperatures according to the invention, which favor the formation of 2-hydroxymethylphenol, it is established that, after reaction times which are otherwise optimum for the formation of 2-hydroxymethylphenol, neither 2-hydroxymethylphenol nor 2-alkylthiomethylphenol have been formed in a significant yield. In other words, this means that the catalyst action which is known for the phenol/formaldehyde reaction is virtually lost when the mercaptan is simultaneously present. In view of the previous findings, it was not to be expected and was very surprising that the catalysts become active again at the temperatures according to the invention and that the reaction to give the 2-alkylthiomethylphenol even proceeds selectively, without substantial resinification.

The process according to the invention exhibits a number of advantages, only some of which will be mentioned in this text: Because the process only consists of one stage, the considerable effort hitherto required for the preparation of a definite intermediate compound is avoided. The running of the reaction does not present problems and the reaction parameters can be freely chosen within wide limits. The yields are high and short reaction times, and hence also high space/time yields, can be achieved by choosing correspondingly high temperatures. The use of a corresponding excess of phenol enables the process to be carried out without applying pressure, even in the case of mercaptans having a low boiling point. The catalysts are readily available industrially and only need to be added in very small amounts. The water formed as co-product is easy to separate off by distillation. The starting materials do not need to be anhydrous. No particular corrosion problems occur.

When ethylmercaptan, formaldehyde and phenol are used as the starting compounds, the reaction can be represented by the following equation:

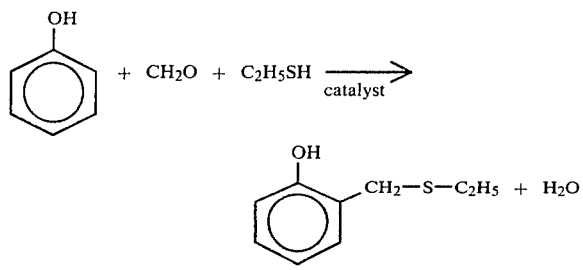

Formula (II) provides a general definition of the phenols to be used as the starting material. Preferred starting material of formula (II) are those in which the radical(s) $R^1$ independently of one another represent a hydrogen atom, a straight-chain or branched alkyl group having 1 to 6 carbon atoms, a cycloalkyl group having 3 to 6 carbon atoms, a phenyl, benzyl or $C_1$ to $C_4$ alkoxy radical or a halogen atom. Phenols in which n is 1 and $R^1$ has the abovementioned general and preferred meanings are particularly preferred as the starting materials of formula (II). Phenol itself (i.e. formula (II) in which n is 1 and $R^1$ is hydrogen) is very particularly preferred as a starting material of formula (II).

Phenols of the formula (II) are known and can be prepared by known processes (see Houben-Weyl, Volume 6/1c, 4th edition, 1976).

Formula (III) provides a general definition of the mercaptans to be used according to the invention as starting materials. Particularly preferred starting material of formula (III) are those in which the radical $R^2$ represents a straight-chain or branched alkyl group having 1 to 12 carbon atoms or an alkoxy-substituted alkyl group, a cycloalkyl group having 3 to 6 carbon atoms, a phenyl or benzyl radical or an alkyl- and/or halogen-substituted phenyl radical.

Mercaptans of the formula (III) are in themselves known and can be prepared analogously to known processes.

The formaldehyde to be used as a starting material can be used in various forms, for example as a gas dissolved in a solvent, in polymeric form or also in the form of formaldehyde-producing compounds (see J. F. WALKER: "Formaldehyd" ("Formaldehyde") 3rd edition, 1964, Reinhold Publishing Corp.). Aqueous formaldehyde solutions (formalin) or paraformaldehyde are preferably used.

The formaldehyde can also be used together with the appropriate mercaptan, in the form of the thiomethanol (half-mercaptal) which forms when these two compounds react. For the formation of such thiomethanols, see T. G. LEVI, Gazz. chim. ital. 62 (1932) 775–780; and H. BÖHME and H. P. TELZ Ann. Chem. 620 (1959) 1–4.

When carrying out the process, generally at least about 0.8 mole of the appropriate phenol are used per mole of formaldehyde. In the case of phenols having two free ortho-positions, it is particularly advantageous to use a molar ratio of phenol/formaldehyde of more than 0.8, because the introduction of a second alkyl- or aryl-thiomethyl group into the 6-position of the phenol is thereby opposed and dilution of the reaction medium, which favors the reaction from a technical point of view, is simultaneously achieved. Thus, there are no upper limits to the phenol/formaldehyde ratio. For practical reasons, the reaction is usually carried out with phenol/formaldehyde molar ratios of between about 1 and 20, in particular between about 1.5 and 15.

When carrying out the process according to the invention, the amount of mercaptan to be used per 1 mole of formaldehyde can vary within wide limits. Usually, the reaction is carried out with amounts of about 1 mole of mercaptan per mole of formaldehyde. Since the mercaptan can also simultaneously be used as the solvent, there are also no upper limits to the mercaptan/formaldehyde ratio.

Apart from the appropriate phenol and the appropriate mercaptan, any other inert protic or aprotic solvent can be used as the diluent in the process according to the invention.

Amongst the metal compounds mentioned as catalysts for the process according to the invention, lithium, magnesium, calcium, strontium, barium, zinc, cadmium, lead, manganese and/or cobalt compounds have proved particularly suitable.

The amounts in which the catalysts to be used according to the invention are employed can vary within wide limits. The catalyst action is already clearly noticeable when $5 \times 10^{-6}$ mole of metal compound is added per mole of phenol. It is also possible to use 0.1 mole of metal compound, or more, per mole of phenol, but the addition of these large amounts does not generally offer any advantage. In general, the addition of $1 \times 10^{-5}$ to $1 \times 10^{-2}$ mole, in particular about $5 \times 10^{-5}$ to $5 \times 10^{-3}$ mole, of metal compound per mole of phenol has proved suitable.

The metal compounds to be used according to the invention as the catalyst can be used in the form of inorganic or organic compounds, for example in the form of their oxides, hydrated oxides, hydroxides, carbonates, nitrates, sulphides, sulphites, sulphates, phosphates, borates, plumbates, chromates, manganates, formates, acetates, propionates, valerates, oxalates, benzoates, salicyclates, tartrates, lactates, citrates, alcoholates, phenolates or mercaptides, optionally containing water of hydration, or also, for example, as alkyl or aryl compounds of the appropriate metals. If appropriate, the phenolates can also be prepared in situ, before the actual reaction, from the appropriate metal and the phenol, which is still dry.

Where metal compounds of lead, manganese, cobalt, nickel, iron and/or chromium, are to be used in the process according to the invention, these metals can be present in various oxidation states.

The metal compound to be used is chosen primarily with regard to practical considerations, for example with regard to the availability. The metal compounds are preferably used in the form of their oxides, hydroxides, carbonates, formates, acetates or phenolates. Of course, it is also possible to use combinations of the catalysts according to the invention.

The metal compound can be added to the reaction components as a solid, preferably in a finely divided form, or in the form of a solution or suspension. The solvents or suspension agents can be phenol, the appropriate mercaptan or any other inert protic or aprotic substances, for example water, methanol, ethanol, propanol, cyclohexane, toluene or chlorobenzene.

The metal compound can undergo modifications throughout the process according to the invention and also does not need to be completely soluble in the reaction medium. For example, the modification of the metal compound used can also be associated with a change in the oxidation state of the metal.

The process according to the invention is usually carried out by heating a mixture of phenol, formaldehyde or formaldehyde-producing compound, and mercaptan to a temperature of 90° C. or above, and keeping it at $\geq 90°$ C. until the reaction to give the 2-alkyl- or 2-aryl-thiomethylphenol has taken place to the desired extent. The reaction, as stated previously, is carried out at temperatures of 90° C. to 220° C., preferably about 100° to 200° C.

The required reaction time can easily be monitored analytically, for example, via the conversion of mercaptan, determined by volumetric analysis, or via the formation of 2-alkyl- or 2-aryl-thiomethylphenol, determined by gas chromatography or high-pressure liquid chromatography.

The reaction can be carried out at normal pressure, for example also under reflux, or under autogenous pressure in an autoclave. The procedure depends on the vapor pressure of the reaction mixture, the technical factors and the desired reaction time. Working under autogenous pressure in an autoclave permits higher reaction temperatures and hence shorter reaction times. The procesure using an autoclave can be advantageous in the case of low-boiling mercaptans. Excess phenol and/or high-boiling inert diluent make it possible to work at higher temperatures, even under normal pressure.

The catalyst, phenol, mercaptan and formaldehyde or formaldehyde-producing component are usually mixed at a temperature which is below the temperature range of 90° to 220° C., claimed according to the invention, for example at 15° to 90° C. or 40° to 80° C. The above-mentioned components can be brought together in any order. For example, it has proved suitable initially to add the catalyst to a warm melt of the phenol, at 50° to 80° C., and then to add the formaldehyde and finally the mercaptan, and subsequently to heat the mixture to the temperatures according to the invention. However, it is also possible to change the order of addition of the catalyst, formaldehyde and mercaptan to no disadvantage. Of course, it is also possible to mix two, three or all four components simultaneously. The formaldehyde and the mercaptan, in the form of the appropriate thiomethanol (half-mercaptal), can also be metered into the phenol/catalyst mixture or a reverse order can also be chosen. Naturally, it is also possible to mix the components at one of the temperatures according to the invention; however, in this case, greater attention must be paid to the metering times under certain circumstances. If the formaldehyde is added to the phenol/-catalyst mixture before the mecaptan, the mercaptan should generally be added more rapidly, the higher is the temperature of the mixture.

The 2-alkyl- or 2-aryl-thiomethylphenol formed is isolated by separating off the unreacted or excess phenol, and the diluent which may have been used concomitantly, by known methods. The unreacted or excess phenol can be re-used in the reaction according to the invention and the same applies to the diluent which may have been used concomitantly. If appropriate, by-products are to be wholly or partially removed by current methods. The water obtained as a by-product can also be wholly or partially removed during the reaction.

The alkyl- and aryl-thiomethylphenols which can be prepared by the process according to the invention can be used as intermediates for the synthesis of plant protection agents, in particular insecticidal active compounds, for example, (2-ethylthiomethylphenyl) N- methyl-carbamate (see DT-PS (German Patent) No. 1,910,588 and DE-OS (German Published) No. 2,122,311).

PREPARATIVE EXAMPLES

EXAMPLE 1

0.85 g of zinc acetate ( $\Delta$ 0.00465 mole of $Zn^{++}$), in the form of an approximately 20% strength aqueous solution, was added to 564 g (6 moles) of molten phenol at about 75° C., in a flask equipped with an internal thermometer, a reflux condenser and a stirrer, and then 30 g of paraformaldehyde containing 4% of water ($\Delta$ 0.96 mole of $CH_2O$) and finally 62 g of approximately 97% pure ethylmercaptan ($\Delta$ 0.97 mole) were added. The mixture was then heated to about 135° C. in the course of 0.5 hour. Reflux commenced at this temperature. After a total of 6 hours at 135° C.$\pm$5°, the mixture was cooled. At this point, the conversion of ethylmercaptan was 98%, determined by iodometry, the yield of 2-ethylthiomethylphenol was 86% of theory, relative to formaldehyde, determined by gas chromatography, and the ratio of 2- to 4-ethylthiomethylphenol was 98.9:1.1. On subsequent mild fractionation in vacuo over a Vigreux column, 131.5 g of >98% pure 2-ethylthiomethylphenol distilled over at an overhead pressure of <2 mbars, after the water of reaction and excess phenol.

EXAMPLE 2 (COMPARISON EXAMPLE)

If a mixture, prepared as in Example 1 and consisting of 6 moles of phenol, 0.00465 mole of zinc acetate, 0.96 mole of formaldehyde (as paraformaldehyde) and 0.97 mole of ethylmercaptan, was stirred at 75° C., the yields of 2-ethylthiomethylphenol (2-ETMP) and 2-hydroxymethylphenol (2-HMP), determined by gas chromatography, and also the conversions of ethylmercaptan, determined by iodometry, after certain times, were given in Table 1:

TABLE 1

| | Yield and conversions at 75° C. after | | | | |
|---|---|---|---|---|---|
| | 6 | 24 | 48 | 96 | 200 hours |
| yield of | | | | | |
| 2-HMP | 6 | 6 | 6 | 6 | 6% of theory |
| 2-ETMP | 1.5 | 3.5 | 6.5 | 12 | 23% of theory |
| Conversion of ethylmercaptan | 6 | 9 | 14 | 23 | 43% |

After 6 hours at 75° C., the same experiment, carried out without adding ethylmercaptan, gave a yield of 2-HMP of 75–80%.

It was seen that, on the one hand, the formation of 2-HMP, catalyzed by zinc acetate, was virtually stopped by adding ethylmercaptan, but that, on the other hand, no significant amount of 2-ETMP was formed, even with very long reaction times. The conversion of ethylmercaptan was approximately twice as high as the formation of ETMP.

In contrast, at the temperatures according to the invention, 2-ETMP was obtained in a very short time (6 hours) with a high selectivity and in a high yield (86% of theory) (compare Example 1).

EXAMPLE 3

92 g of a reaction product of formaldehyde and ethylmercaptan (ethylthiomethanol), obtained in accordance with the instructions of T. G. LEVI, Gazz. chim. ital. 62 (1932), page 777, were added to a solution, kept at 130°–135° C., of 4 ml of 20% strength zinc acetate solution in 640 g (6 moles) of phenol. After 6 hours at an internal temperature of 130° to 135° C., gas chromatographic analysis of the reaction mixture showed a yield of 2-ethylthiomethylphenol of 85% of theory (relative to ethylthiomethanol) and a ratio of 2-/4-ethylthiomethylphenol of 98.5:1.5.

EXAMPLES 4 TO 26

The procedure followed was as in Example 1, except that different catalysts were used. The molar ratio of phenol:formaldehyde:ethylmercaptan was 6:0.96:0.97. Paraformaldehyde containing 4% of water was used as the formaldehyde. The amount of catalyst in moles per mole of phenol could be taken from Table 2, and the same applied to the reaction temperature, the reaction time, the conversion of ethylmercaptan, the yield of 2-ethylthiomethylphenol (2-ETMP), relative to formaldehyde, and the ratio of 2-ethylthiomethylphenol (2-ETMP) to 4-ethylthiomethylphenol (4-ETMP). The ratio of 2-/4-ETMP was a measure of the ortho-selectivity.

Examples 4 to 6 are comparison examples which show that, at the temperatures according to the invention, without using a catalyst (Example 4) or using catalysts other than those according to the invention, the yields of 2-ETMP were smaller, but that, in particular, the ortho-selectivities were substantially poorer.

TABLE 2

Influence of various catalysts on the conversion of phenol/formaldehyde/ethylmercaptan to 2-ethylthiomethylphenol (2-ETMP)

| Example No. | Catalyst Form of addition | Catalyst Mole/mole of phenol | Reaction temperature [°C.] | Reaction time [hours] | Conversion of mercaptan [%] | Yield of 2-ETMP (relative to $CH_2O$) [%] of theory | Ratio 2-ETMP:4-ETMP |
|---|---|---|---|---|---|---|---|
| 4[a] | none | — | 135–140 | 6 | 99 | 45 | 82:18 |
| 5[a] | triethylamine | $1.7 \cdot 10^{-3}$ | 122–136 | 6 | 97 | 62 | 74:26 |
| 6[a] | KOH | $2.8 \cdot 10^{-3}$ | 116–131 | 6 | 95 | 68 | 82:18 |
| 7 | LiOH | $7.7 \cdot 10^{-4}$ | 107–130 | 8 | 94 | 79 | 95:5 |
| 8 | $Mg(OCOCH_3)_2$ | $1 \cdot 10^{-3}$ | 116–133 | 8 | 96 | 81 | 99:1 |
| 9 | $Ca(OCOCH_3)_2$ | $\sim 5 \cdot 10^{-4}$ | 122–125 | 8 | 82 | 55[b] | 98:2 |
| 10 | $Sr(OH)_3$ | $7.6 \cdot 10^{-4}$ | 105–128 | 8 | 91 | 52[b] | 97:3 |
| 11 | $Ba(OCOCH_3)_2$ | $\sim 7 \cdot 10^{-4}$ | 131–133 | 7 | 96 | 70 | 96.7:3.3 |
| 12 | $Pb(OCOCH_3)_2$ | $7.6 \cdot 10^{-4}$ | 128–135 | 6 | 98 | 85 | 98.7:1.3 |
| 13 | ZnO | $7.8 \cdot 10^{-4}$ | 130–136 | 8 | 99 | 86 | 98.2:1.8 |
| 14 | $Cd(OCOCH_3)_2$ | $7.6 \cdot 10^{-4}$ | 130–136 | 8 | 97 | 82[b] | 97.6:2.4 |
| 15 | $Cu(OCOCH_3)_2$ | $7.6 \cdot 10^{-4}$ | 130–136 | 5 | 93 | 60 | 93:7 |
| 16 | $Fe_2O_3$ | $3,8 \cdot 10^{-4}$ | 131–139 | 7 | 93 | 65 | 93:7 |
| 17 | $Co(OCOCH_3)_2$ | $7.6 \cdot 10^{-4}$ | 131–136 | 6 | 97 | 75 | 93:3 |

TABLE 2-continued

Influence of various catalysts on the conversion of phenol/formaldehyde/ethyl-mercaptan to 2-ethylthiomethylphenol (2-ETMP)

| Ex-ample No. | Catalyst Form of addition | Mole/mole of phenol | Reaction temperature [°C.] | Reaction time [hours] | Conversion of mercaptan [%] | Yield of 2-ETMP (relative to CH$_2$O) [%] of theory | Ratio 2-ETMP:4-ETMP |
|---|---|---|---|---|---|---|---|
| 18 | Ni(OCOCH$_3$)$_2$ | 7.6.10$^{-4}$ | 133–137 | 6 | 99 | 56 | 92:8 |
| 19 | Cr(OH)$_3$ | 7.6.10$^{-4}$ | 129–136 | 7 | 98 | 61 | 91:9 |
| 20 | Mn(OCOCH$_3$)$_2$ | 7.6.10$^{-4}$ | 117–133 | 4 | 99 | 85 | 99:1 |
| 21 | Aluminum phenolate | 6.10$^{-3}$ | 124–125 | 8 | 86 | 55$^{(b)}$ | 96.4:3.6 |
| 22 | PbO$_2$ | 6.4.10$^{-4}$ | 123–134 | 7 | 94 | 76 | 97.5:2.5 |
| 23 | Cu$_2$O | 1.2.10$^{-3}$ | 130–138 | 7 | 98 | 60 | 93:7 |
| 24 | FeSO$_4$ | 7.2.10$^{-4}$ | 132–140 | 6 | 98 | 61 | 93:7 |
| 25 | MnO$_2$ | 1.9.10$^{-3}$ | 124–136 | 7 | 98 | 81 | 98.5:1.5 |
| 26 | Al$_2$O$_3$ | 7.5.10$^{-4}$ | 132–138 | 6 | 98 | 61 | 97:3 |

$^{(a)}$Comparison examples
$^{(b)}$The yield was even higher with a longer reaction time
$^{(c)}$Temperature of the reaction mixture under reflux at normal pressure

EXAMPLES 27 TO 32

The yields of 2-ethylthiomethylphenol (2-ETMP), obtained with zinc at various concentration ratios and temperatures, the ratios of 2-ETMP to 4-ETMP and also the conversions of ethylmercaptan are summarized in Table 3. As also in the rest of the Examples, the ETMP was determined by gas chromatography and the conversion was determined by iodometry. The formaldehyde used was in the form of paraformaldehyde containing 4% of H$_2$O and the zinc used was in the form of a 20% by weight aqueous zinc acetate solution.

EXAMPLE 33

4.5.10$^{-3}$ mole of zinc acetate, in the form of an approximately 20% strength aqueous solution, 30 g of 96% pure paraformaldehyde ( 0.96 mole of CH$_2$O) and 113.6 g of 97% pure thiophenol (1 mole) were added to 564 g (6 moles) of phenol at about 70° C. The mixture was then heated to the reflux temperature in the course of about 30 minutes and kept under these conditions for 7.5 hours (temperature of the mixture 154° to 132° C.). After this time, gas chromatography analysis gave a yield of 2-phenylthiomethylphenol of 81% of theory (relative to formaldehyde) and a ratio of 2- to 4-phenylthiomethylphenol of more than 99:1. The 2-phenylthiomethylphenol obtained on subsequent distillation at 140°–150° C./0.6–0.9 mm Hg was 98% pure.

may be made without departing from the spirit and scope of the present invention.

We claim:

1. In the preparation of a 2-alkyl- and 2-aryl-thiomethylphenol of the formula

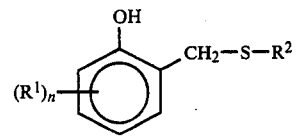

in which
R$^1$ is, or the radicals R$^1$ are, in the 3-, 5- and/or 6-positions relative to the hydroxyl group and each independently is a hydrogen or halogen atom, an alkyl group having 1 to 6 carbon atoms, a cycloalkyl group having 3 to 6 carbon atoms, or a phenyl, benzyl or C$_1$ to C$_4$-alkoxy radical,
n is 1, 2, or 3, and
R$^2$ is an alkyl group having 1 to 12 carbon atoms, an alkoxy-substituted alkyl group, a cycloalkyl group having 3 to 6 carbon atoms, a phenyl or benzyl group or an alkyl- and/or halogen-substituted phenyl group,
by reacting a phenol or the formula

TABLE 3

Influence of the concentration ratios and temperatures on the formation of 2-ethylthiomethylphenol

| Ex-ample No. | Zinc concentration Moles/mole of phenol | Phenol moles | CH$_2$O moles | C$_2$H$_5$SH moles | Temperature °C. | Time hours | Conversion of mercaptan % | Yield of 2-ETMP relative to CH$_2$O [%] of theory | Ratios 2-ETMP:4-ETMP |
|---|---|---|---|---|---|---|---|---|---|
| 27 | 1.9.10$^{-4}$ | 6 | 0.96 | 0.97 | 134–142$^{(a)}$ | 8 | 98 | 90 | 98.5:1.5 |
| 28 | 1.5.10$^{-3}$ | 6 | 0.96 | 0.97 | 127–135$^{(a)}$ | 6 | 98 | 85 | 98:2 |
| 29 | 7.7.10$^{-4}$ | 4 | 0.96 | 0.97 | 125–137$^{(a)}$ | 7 | 98 | 76 | 98:2 |
| 30 | 7.7.10$^{-4}$ | 10 | 0.96 | 0.97 | 140–143$^{(a)}$ | 2.5 | 98 | 94 | 98.9:1.1 |
| 31 | 7.5.10$^{-4}$ | 6 | 0.96 | 0.97 | 100 | 52 | 97 | 83 | 96.3:3.7 |
| 32 | 7.5.10$^{-4}$ | 6 | 0.96 | 0.87 | 170$^{(b)}$ | 1 | 95 | 87 | 97.5:2.5 |

$^{(a)}$Temperature of the reaction mixture under reflux
$^{(b)}$Under autogenous pressure in a steel autoclave It will be appreciated that the instant specification and examples are set forth by way of illustration and not limitation, and that various modifications and changes

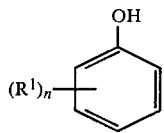

with formaldehyde or a formaldehyde producing compound and with a mercaptan or a thiophenol of the formula $R^2-S-H$, the improvement which comprises effecting the reaction at a temperature of about 90° to 220° C. in the presence of at least one compound of lithium, magnesium, calcium, strontium, barium, zinc, cadmium, lead, manganese, cobalt, nickel, copper, iron, chromium and aluminum as a catalyst.

2. A process according to claim 1, wherein the reaction is carried out in the presence of about 0.1 to $5 \times 10^{-6}$ mole of catalyst compound per mole of phenol.

3. A process according to claim 1, wherein the reaction is carried out in the presence of about $1 \times 10^{-2}$ to $1 \times 10^{-5}$ mole of catalyst compound per mole of phenol.

4. A process according to claim 1, wherein the catalyst comprises at least one compound of lithium, magnesium, calcium, strontium, barium, zinc, cadmium, manganese, lead and cobalt.

5. A process according to claim 1, wherein n is 1.

6. A process according to claim 5, wherein $R^1$ is a hydrogen atom.

7. A process according to claim 1, wherein the reaction is effected at about 100° to 200° C.

8. A process according to claim 3, wherein the catalyst comprises at least one compound of lithium, magnesium, calcium, strontium, barium, zinc, cadmium, manganese, lead and cobalt, $R^1$ is a hydrogen atom, n is 1, and the reaction is effected at about 100° to 200° C.

9. A process according to claim 1, wherein the catalyst comprises at least one compound of magnesium, calcium, strontium, barium, zinc, cadmium, lead, manganese, cobalt, nickel, copper, iron, chromium or aluminum.

* * * * *